United States Patent [19]

Kowar

[11] Patent Number: 5,731,435
[45] Date of Patent: Mar. 24, 1998

[54] PROCESS FOR THE PREPARATION OF HETEROCYCLIC ALKYLAMIDE DERIVATIVES

[75] Inventor: Thomas Robert Kowar, Mt. Prospect, Ill.

[73] Assignee: G. D. Searle & Co., Chicago, Ill.

[21] Appl. No.: 433,622

[22] Filed: May 3, 1995

[51] Int. Cl.$^6$ .................... C07D 211/32; C07D 265/30; C07D 207/08; C07D 207/46
[52] U.S. Cl. .................... 544/169; 546/233; 546/234; 546/567; 546/568
[58] Field of Search .................... 546/233, 234; 544/169; 548/567, 568

[56] References Cited

U.S. PATENT DOCUMENTS

| | | | |
|---|---|---|---|
| 4,639,524 | 1/1987 | Desai et al. | 546/229 |
| 5,097,035 | 3/1992 | Desai et al. | 546/226 |
| 5,276,155 | 1/1994 | Medich et al. | 546/233 |
| 5,432,284 | 7/1995 | Dygos et al. | 546/230 |

FOREIGN PATENT DOCUMENTS

Wo 95/07273  3/1995  WIPO .................... C07D 295/14

OTHER PUBLICATIONS

Desai, Bipin, et al. "Synthesis and Structure–Activity Relationships of a New Series of Antiarrhythmic Agents: Monobasic Derivatives of Disobutamide", *J. Med. Chem.*, 31:2158–2164 (1988).

*Primary Examiner*—C. Warren Ivy
*Assistant Examiner*—Raymond Covington
*Attorney, Agent, or Firm*—Cynthia S. Kovacevic; Roger A. Williams

[57] ABSTRACT

The present invention relates to a novel process for the preparation of N-heterocyclealkanamide derivatives having the following formula:

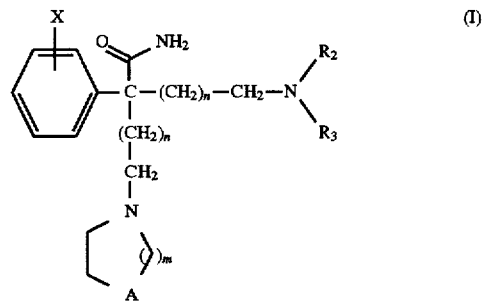

which comprises reacting 1-(2-chloroethyl)piperidine with 2-chlorobenzeneacetonitrile to give (±)-α-(2-chlorophenyl)-1-piperidinebutanenitrile; alkylating the piperidenebutanenitrile to give (±)-α-(2-chlorophenyl)-α-(2,2-dimethoxyethyl)piperidine-1-butanenitrile; hydrolyzing the resulting alkylated piperidinebutanenitrile to give (±)-α-(2-chlorophenyl)-α-(2-oxoethyl)piperidine-1-butanenitrile; reacting the resulting piperidinebutanenitrile with isopropylamine to form (±)-α-(2-chlorophenyl)-α-[2-[(1-methylethyl)imino]ethyl]piperidine-1-butanenitrile; reducing the resulting imine to form (±)-α-(2-chlorophenyl)-α-[2-[(1-methylethyl)amino]ethyl]-piperidine-1-butanenitrile; acetylating the resulting amine to form (±)-N-[3-(2-chlorophenyl)-3-cyano-5-(1-piperidinyl)pentyl]-N-(1-methylethyl)acetamide; hydrolyzing the resulting acetylated amino substituted piperidine butanenitrile to form (±)-α-[2-[acetyl(1-methylethyl)amino]ethyl]-α-(2-chlorophenyl)-1-piperidinebutanamide; and isolating the resulting piperidinebutanamide.

13 Claims, No Drawings

PROCESS FOR THE PREPARATION OF HETEROCYCLIC ALKYLAMIDE DERIVATIVES

BACKGROUND OF THE INVENTION

The present invention relates to a novel process for the preparation of heterocyclic alkylamide derivatives having the following formula:

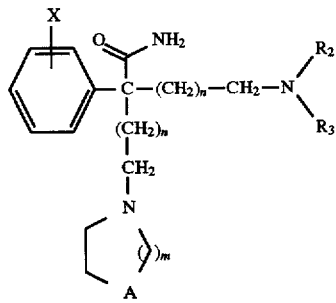

(I)

and the pharmaceutically acceptable acid addition salts thereof wherein X represents halo, alkyl having 1 to 6 carbon atoms, hydrido, trifluoromethyl, phenyl, or lower alkoxy having 1 to 6 carbon atoms; A is selected from $CH_2$ or O; $R_2$ represents alkyl having 1 to 6 carbon atoms; $R_3$ represents acetyl, benzoyl, phenacetyl or trifluoroacetyl; m is an integer selected from 1 or 2; and n is an integer from 1 to 3 inclusive; which comprises reacting 1-(2-chloroalkyl) piperidine with 2-halobenzeneacetonitrile to give 1-(2-halophenyl)-1-piperidinealkanenitrile; alkylating the piperidenealkanenitrile to give α-(2-halophenyl)-α-(2,2-dialkoxyalkyl)-1-piperidinealkanenitrile; hydrolyzing the resulting piperidinealkanenitrile to give α-(2-halophenyl)-α-(2-oxoalkyl)-1-piperidinealkanenitrile; reacting the resulting piperidinealkanenitrile with an alkylamine to form an imine substituted piperidinealkanenitrile; reducing the resulting imine to form an amino substituted piperidinealkanenitrile; acetylating the resulting amine to form an acetylated amino substituted piperidinealkanenitrile; hydrolyzing the resulting acetylated amino substituted piperidinealkanenitrile to form an acetylated amino substituted piperidinealkanamide; and isolating the resulting piperidinealkanamide.

The process of the present invention is especially useful for preparing (±)-α-[2-[acetyl(1-methylethyl)amino]ethyl]-α-(2-chlorophenyl)-1-piperidinebutanamide which is described in U.S. Pat. No. 4,639,524 and is generically referred to as bidisomide. (±)-α-[2-[Acetyl(1-methylethyl)amino]ethyl]-α-(2-chlorophenyl)-1-piperidinebutanamide has antiarrhythmic properties resulting from its electrophysiologic effects in both the upper and lower parts of the heart.

U.S. Pat. No. 4,639,524 discloses a process for preparing monobasic disobutamide derivatives having the following formula:

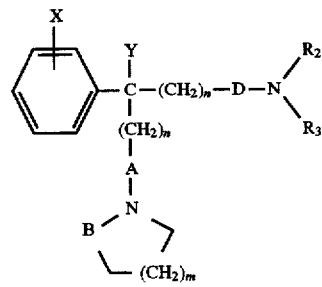

wherein X represents a halo, trifluoromethyl, phenyl, hydrogen, lower alkyl or lower alkoxy substituent; Y represents CN, $CONH_2$, $CON(R_1)_2$ or $CO_2R_1$ where $R_1$ represents lower alkyl; m is the integer 1 or 2 and n is an integer from 1 to 3 inclusive; $R_2$ represents lower alkyl; $R_3$ represents lower alkyl or acetyl, aroyl, phenacetyl or trifluoroacetyl; A, B and D are carbonyl or methylene such that when one of A, B or D is carbonyl the others are methylene and $R_3$ is lower alkyl, whereas when $R_3$ is acetyl, aroyl, phenacetyl or trifluoroacetyl, A, B, and D are methylene.

W095/07273 discloses a process for preparing bidisomide which is outlined in Scheme I.

SCHEME I

Part A

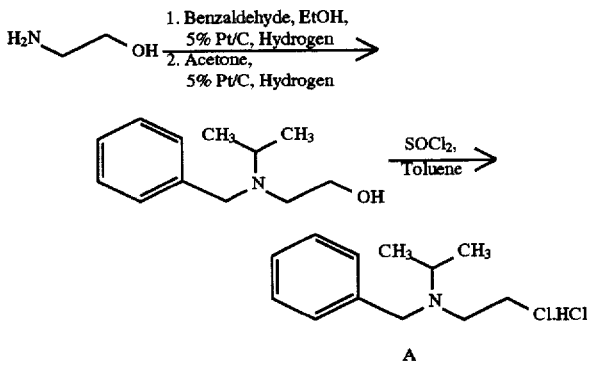

Part B

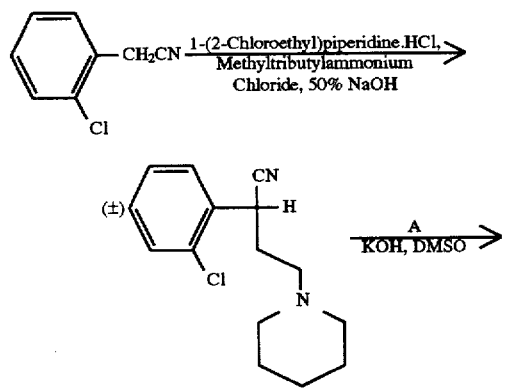

-continued
SCHEME I

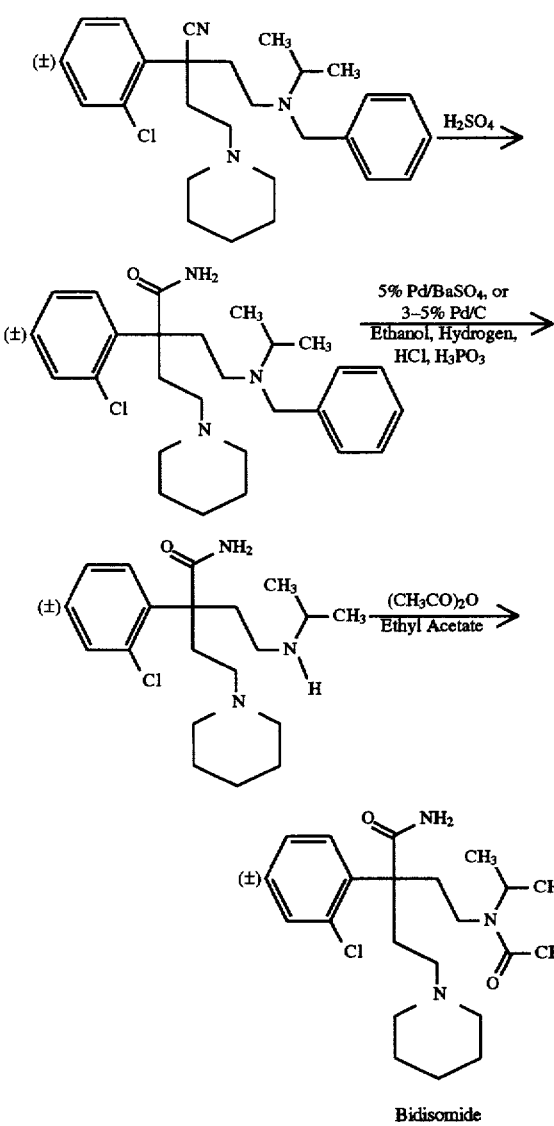

Bidisomide

It would be desirable to provide an alternate process for the preparation of bidisomide which is amenable to scale-up, which employs raw materials which are readily available and inexpensive and which eliminates the hydrogenation reactions and the use of thionyl chloride from the known process.

SUMMARY OF THE INVENTION

The invention herein is directed to a process for the preparation of bidisomide and analogs thereof. The invention includes reacting 1-(2-chloroalkyl)piperidine with 2-halobenzeneacetonitrile to give (±)-α-(2-halophenyl)-1-piperidinebutanenitrile; alkylating the piperidenealkanenitrile to give (±)-α-(2-halophenyl)-α-(2,2-dialkoxyalkyl)-1-piperidinealkanenitrile; hydrolyzing the resulting piperidinealkanenitrile to give (±)-α-(2-halophenyl)-α-(2-oxoalkyl)-1-piperidinealkanenitrile; reacting the resulting piperidinealkanenitrile with an alkylamine to form an imine substituted piperidinealkanenitrile; reducing the resulting imine to form an amino substituted piperidinealkanenitrile; acetylating the resulting amine to form an acetylated amino substituted piperidinealkanenitrile; hydrolyzing the resulting acetylated amino substituted piperidinealkanenitrile to form an acetylated amino substituted piperidinealkanamide; and isolating the resulting piperidinealkanamide.

DETAILED DESCRIPTION OF THE INVENTION

The invention herein is directed to a process for the preparation of a compound of the formula

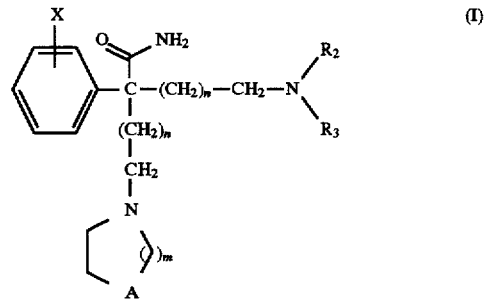

and the pharmaceutically acceptable acid addition salts thereof wherein X represents halo, alkyl having 1 to 6 carbon atoms, hydrido, trifluoromethyl, phenyl, or lower alkoxy having 1 to 6 carbon atoms; A is selected from $CH_2$ or O; $R_2$ represents alkyl having 1 to 6 carbon atoms; $R_3$ represents acetyl, benzoyl, phenacetyl or trifluoroacetyl; m is an integer 1 or 2; and n is an integer from 1 to 3 inclusive. More preferably the invention herein is directed to the synthesis of bidisomide.

A synthetic scheme for the most preferred synthetic method for preparing bidisomide is outlined in Scheme II and the following description thereof.

SCHEME II

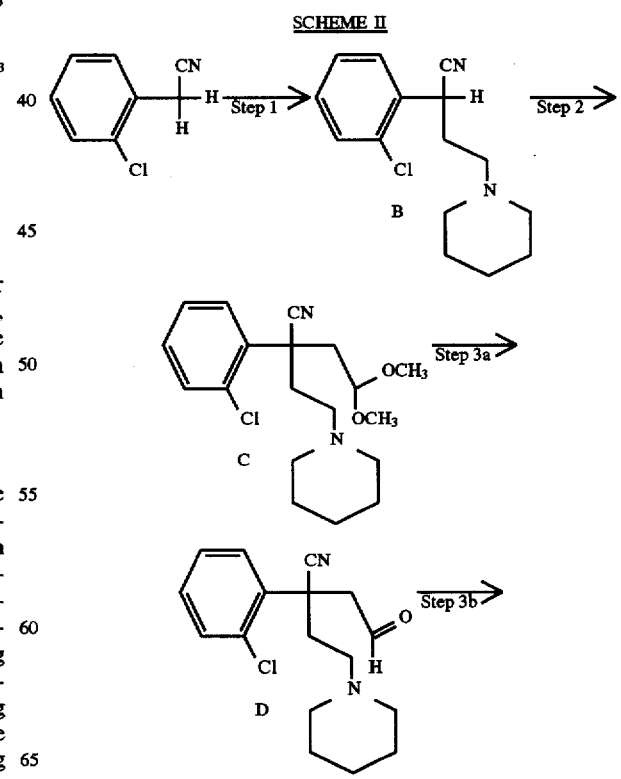

-continued
SCHEME II

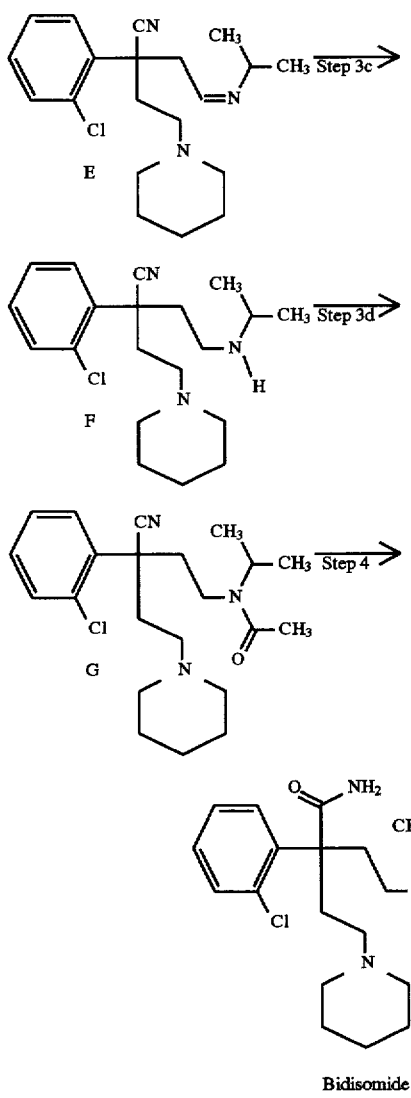

Bidisomide

The synthesis outlined in Scheme II comprises (a) reacting commercially available 2-chlorobenzeneacetonitrile with 1-(2-chloroethyl)piperidine in the presence of a base, such as sodium hydroxide, and methyltributylammonium chloride to give (±)-α-(2-chlorophenyl)-1-piperidinebutanenitrile; (b) alkylating the resulting piperidinebutanenitrile with bromoacetaldehyde dimethyl acetal in dimethylsulfoxide (DMSO) in the presence of potassium hydroxide to produce (±)-α-(2-chlorophenyl)-α-(2,2-dimethoxyethyl)-1-piperidinebutanenitrile; (c) hydrolyzing the resulting piperidinebutanenitrile in a solvent such as toluene with hydrochloric acid to produce (±)-α-(2-chlorophenyl)-α-(2-oxoethyl)-1-piperidinebutanenitrile; (d) reacting the resulting piperidinebutanenitrile with isopropylamine in a solvent such as toluene in the presence of potassium carbonate to form an imine substituted piperidinebutanenitrile; (e) reducing the resulting imine substituted piperidinebutanenitrile with sodium borohydride and ethanol to form an amino substituted piperidinebutanenitrile; (f) acetylating the resulting amino substituted piperidinebutanenitrile with acetic anhydride in a solvent such as toluene to produce an acetylated amino substituted piperidinebutanenitrile; (g) hydrolyzing the resulting acetylated amino substituted piperidinebutanenitrile with sulfuric acid to produce an acetylated amino substituted-1-piperidinebutanamide; and (h) isolating the resulting 1-piperidinebutanamide.

The starting materials for the process of this invention are all commercially available or can be prepared according to conventional methods known to those with skill in the art.

Generally, the first step (Step 1) of the process of the present invention is carried out by reacting a commercially available halobenzeneacetonitrile with 1-(2-haloalkyl) N-containing heterocycle in the presence of base and methyltributylammonium chloride at a temperature ranging from 30° C. to 70° C. and most preferably at 40° heating to 60°. Suitable bases are exemplified by sodium hydroxide, or potassium hydroxide, with sodium hydroxide being preferred.

The alkylating step (Step 2) is carried out at a temperature ranging from 30° C. to 70° C. with a temperature ranging from 30° C. to 40° C. being preferred using an alkylating agent in the presence of base and DMSO. Suitable alkylating agents are exemplified by bromoacetaldehyde dimethyl acetal, chloroacetaldehyde dimethylacetal, 2-(2-bromoethyl)-1,3-dioxolane, chloroacetaldehyde diethylacetal or bromoacetaldehyde diethylacetal with bromoacetaldehyde dimethyl acetal being preferred. Suitable bases are potassium hydroxide, or sodium hydroxide with potassium hydroxide being preferred.

Hydrolysis of the piperidinealkanenitrile (Step 3a) is carried out in the presence of hydrochloric acid in an inert solvent. Suitable inert solvents are exemplified by toluene, xylene and heptane, with toluene being preferred.

The product of Step 3a of the process is reacted with an alkylamine in a solvent and dried with potassium carbonate (Step 3b). For the preparation of bidisomide the alkylamine is isopropylamine. Suitable solvents are exemplified by toluene, xylene and heptane, with toluene being preferred.

Reduction (Step 3c) of the product of Step 3b is carried out with sodium borohydride and ethanol.

The product of Step 3c is acylated with an acylating agent such acetic anhydride in a solvent (Step 3d). Suitable solvents include toluene, xylene and heptane, with toluene being preferred.

The product of Step 3d is then hydrolyzed (Step 4) using sulfuric acid to produce the desired end product. The end product is then isolated and recovered using conventional methodology.

More generally the process can be varied by substituting various reactants and reagents which are known by those with skill in the art which are commercially available reactants or reagents or reactants which can be prepared by conventional methodology. For example, in Step 1, the haloalkyl piperidene can be replaced with a haloalkylpyrrolidine or haloalkylmorpholine to produce a pyrrolidinealkanamide or morpholinealkanamide respectively. Alternatively, various alkylating reagents can be used in Step 2 to form alkyl chains of varying length. Likewise in Step 3b any suitable alkylamine can be substituted for the isopropylamine used in the preferred product.

As used herein, the term "alkyl", embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenyloxy, 3-methylbutoxy, 1-methylbutoxy, 1-ethylpropoxy, 2,2-dimethylpropoxy, 1,1-dimethylpropoxy, hexenyloxy, and 4-methylpentoxy.

As used herein the term "halo" embraces halogen atoms. Illustrative of such atoms are chloro (Cl), fluoro (F), bromo (Br) and iodo (I).

As used herein the term "N-containing heterocycle" refers to a 5 or 6 membered ring wherein at least one carbon atom in the ring is replaced by a nitrogen and wherein one carbon may optionally be replaced by an oxygen. Illustrative of such "N-containing heterocycles" are piperidine, pyrrolidine, morpholine and the like.

The present invention provides a safe, convenient and cost effective manufacturing process for the production of the alkylamide derivatives of the formula I. More particularly it provides a safe, convenient and cost effective manufacturing process for the production of (±)-α-[2-[acetyl(1-methylethyl)amino]ethyl]-α-(2-chlorophenyl)-1-piperidinebutanamide. Its safety is demonstrated by the elimination of potentially hazardous hydrogenation steps and by elimination of the use of the hazardous reagent thionyl chloride. The process utilizes raw materials which are readily available and cost efficient. Its convenience is demonstrated by the synthetic route comprising a limited number of steps. Its cost effectiveness is demonstrated by the final product being produced in high yield and high quality.

The following specific examples of reaction steps further illustrate the invention. All temperatures herein are degrees Celsius unless otherwise noted.

Chemical reactions are monitored by gas chromatography (GC) or thin layer chromatography (TLC). Chemical intermediates are analyzed by GC or high performance liquid chromatography (HPLC). Qualitative estimates of purity are made based upon integration of the area under the peaks in the GC or HPLC chromatograms.

GC Method
Column: Methyl Silicone (10 m×0.53 mm)
Temperature: 80° C. for 2 min, 80°–275° C. at 50° C./min with an 8-min hold at 275° C.
Flow Rate: 5 mL/min (helium)
Detection: Flame ionization HPLC Method A
Column: Supelco LC-DP (250 mm×4.6 mm i.d., 5 micron particle size)
Column Temperature: 40° C.
Mobile Phase: Tetrahydrofuran/pH 3.0 triethylamine phosphate (TEAP), 5 mM HEPTSA, 11/89 (V/V)
Flow Rate: 1.5 mL/minute
Injection Volume: 15 microliters
Sample concentration: 1.0 mg/mL
Detection: UV at 210 nm
Pressure: 2000 psi
Run Time: 45 minutes HPLC Method B
Column: Supelco LC-DP (250 mm×4.6 mm i.d., 5 micron particle size)
Column Temperature: 40° C.
Mobile Phase: Tetrahydrofuran/pH 3.0 triethylamine phosphate with 5 mM HEPTSA, 11/89 (V/V)
Flow Rate: 1.0 mL/minute
Injection Volume: 15 microliters
Sample concentration: 1.0 mg/mL
Detection: UV at 210 nm
Pressure: 1500 psi
Run Time: 45 minutes TLC Method
Adsorbent: DC-Fertigplatten SIL G-25 UV$_{254}$
Mobile Phase: Chloroform/Methanol/Ammonium Hydroxide, 85/14/1 (v/v/v)
Visualization: I$_2$ and SWUV The following non-limiting example describes and illustrates a method for carrying out the process of the present invention, as well as other aspects of the invention, and the results achieved thereby in further detail. Both an explanation of, and the actual procedures for, the various aspects of the present invention are described where appropriate. This example is intended to be merely illustrative of the present invention, and not limiting thereof in either scope or spirit. Those of skill in the art will readily understand that known variations of the conditions and processes described in this example can be used to perform the process of the present invention. Unless otherwise indicated all starting materials and equipment employed were commercially available.

Step 1

Preparation of (±)-α-(2-Chlorophenyl)-1-piperidinebutanenitrile (Step 1)

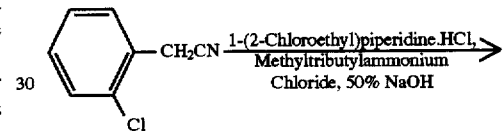

To a reaction vessel under a nitrogen atmosphere was charged 756.6 kg of sodium hydroxide solution (50% w/w), 220.6 kg of 1-(2-chloroethyl)piperidine, monohydrochloride, 199.0 kg of 2-chlorobenzeneacetonitrile, and 4.2 kg of methyltributylammonium chloride (75% w/w in water). The reaction mixture was heated to 40° C. and was stirred for 6 hours and then heated to 60° C. for 6 hours. When the reaction was complete as indicated by GC, the reaction mixture was cooled to 25° C. The reaction mixture was diluted with 996 L of water and 396 L of toluene and stirred for 1 hour. After separation of the layers, the organic phase was extracted with 789 L of hydrochloric acid, 2N. The acidic extract was washed twice with 151 L of toluene at 50° C., basified with 136.9 kg of sodium hydroxide solution (50% w/w) to a pH>12 and extracted twice with a total of 1,103 L of heptane (or mixed heptanes). The combined organic phase was washed with 100 L of water and filtered through a layer of powdered cellulose. The solvent was removed by distillation under reduced pressure to give 310.2 kg (86.36% pure by HPLC Method A, 77.6% yield) of an oil which was (±)-α-(2-chlorophenyl)-1-piperidine-butanenitrile (B).

Step 2

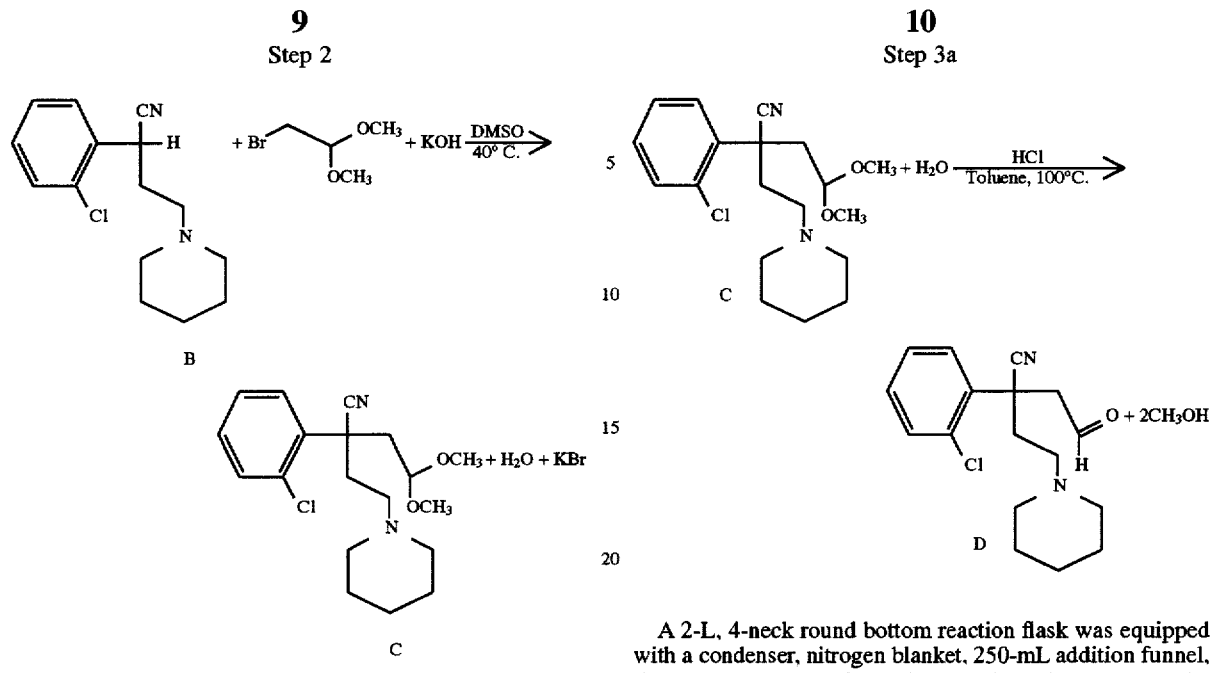

A 5-L, 3-neck round bottom reaction flask was equipped with a condenser, 1-L addition funnel, thermometer, mechanical stirrer, heating mantle, thermowatch, and nitrogen blanket. The reaction flask was purged with nitrogen. The reaction vessel was charged with potassium hydroxide, 134.79 g (2.162 moles), and dimethylsulfoxide, 1000 mL. The reaction mixture was stirred and heated to 30° C. for 15 minutes. The reaction flask was charged with B, 284.04 g from the previous reaction. The reaction mixture exothermed to 40° C. The reaction flask was cooled to 30° C. Dimethylsulfoxide, 250 mL, was used to rinse the flask that contained B, and the rinse was charged to the reaction mixture. Bromoacetaldehyde dimethyl acetal, 200.97 g (1.02 moles), was charged to the reaction mixture at a rate such that the temperature remained at less than 40° C. Addition was completed in one hour. The reaction mixture was stirred for 1.5 hours at 40° C. The reaction mixture was sampled for GC analysis for completion of reaction. The reaction was considered complete when the area of integration of B was less than 1%. At this point the reaction was not complete. Bromoacetaldehyde dimethyl acetal, 9.13 g (0.05 mole), was charged to the reaction mixture at a rate such that the temperature remained at less than 40° C. The reaction mixture was sampled for GC analysis for completion of reaction. At this point the reaction was complete. The product mixture was cooled to ambient temperature, 20°–25° C. Cooled water 1 L, was charged to the 1-L addition funnel and added to the reaction mixture at a rate such that the temperature remained less than 25° C. Heptane, 800 mL, was charged to the reaction mixture. The reaction mixture was stirred for 15 minutes. The phases were separated. The aqueous phase was extracted with 800 mL heptane. The phases were separated. The organic phases were combined. The organic phase was dried over potassium carbonate, 50 g (0.362 moles). The mixture was filtered and the filtrate was stripped of solvent under vacuum at 50° C. The crude product (±)-α-(2-chlorophenyl)-α-(2,2-dimethoxyethyl)piperidine-1-butanenitrile, C was recovered as a viscous red oil 336.6 g (87.4% pure by HPLC method B, 89.9% yield).

Step 3a

A 2-L, 4-neck round bottom reaction flask was equipped with a condenser, nitrogen blanket, 250-mL addition funnel, thermometer, mechanical stirrer, and heating mantle. The reaction flask was purged with nitrogen. The product of Step 2, C, from the previous reaction, 35.0 g (0.10 mole), was dissolved in toluene, 200 mL. Water, 250 mL (13.873 moles), was charged to the reaction flask. Hydrochloric acid, 15 mL (0.179 mole), was charged to the reaction flask. The solution of C in toluene was then charged to the reaction flask. The reaction mixture was stirred and heated at reflux for 30 minutes. The reaction solution was cooled to less than 5° C. using an ice water bath. Potassium carbonate, 25.0 g (0.181 mole), dissolved in water, 100 mL (5.549 moles), was charged to the reaction mixture at a rate such that the temperature remained less than 5° C. The reaction mixture was stirred for 15 minutes. The phases were separated. The aqueous phase was extracted with 100 mL toluene. The organic phase was separated and combined with the first organic phase. The product (±)-α-(2-chlorophenyl)-α-(2-oxoethyl)-piperidine-1-butanenitrile, D was kept in toluene solution for the next step.

Step 3b

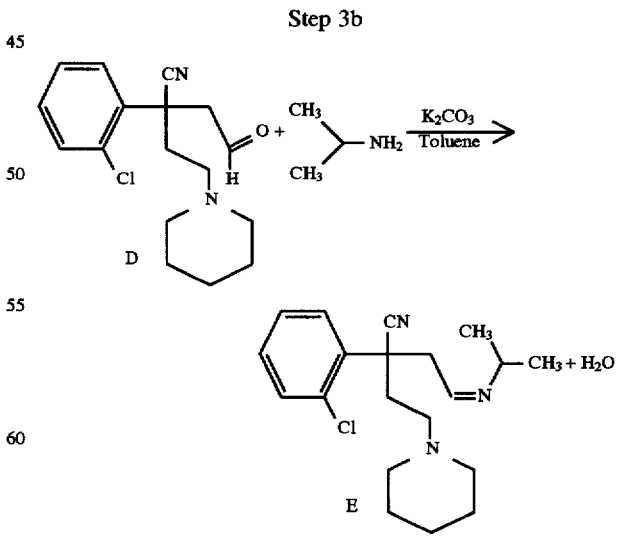

A 1-L, 4-neck round bottom reaction flask was equipped with a condenser, thermometer, mechanical stirrer, and nitrogen blanket. The flask was purged with nitrogen. Potassium carbonate, 15.0 g (0.108 mole) was charged to the reaction flask. The product of Step 3a, D, 30.4 g (0.100 mole), dissolved in toluene, 300 mL, was then charged to the reaction flask. Isopropylamine 20.0 mL (0.235 mole) was charged to the reaction flask. The reaction mixture was stirred for 1 hour. The mixture was filtered and the filter cake was washed with 2×10 mL of toluene. The filtrate was stripped of solvent under vacuum at 40° C. The product (±)-α-(2-chlorophenyl)-α-[2-[(1-methylethyl)imino]ethyl]piperidine-1-butanenitrile, E was recovered as an orange oil, 32.8 g and was carried directly into the next reaction.

Step 3c

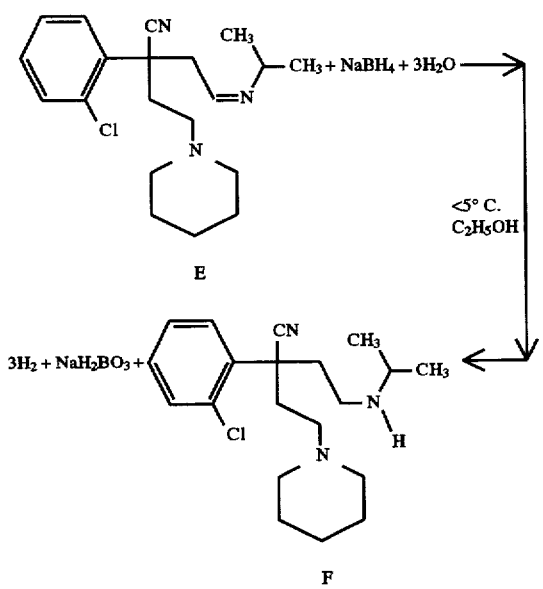

A 2-L, 4-neck round bottom reaction flask was equipped with a condenser, thermometer, mechanical stirrer, ice water bath, 1-L addition funnel, and nitrogen blanket. The flask was purged with nitrogen. Sodium borohydride 7.6 g (0.203 mole) was charged to the reaction flask. The reaction flask was cooled to less than 5° C. using an ice bath. The product from Step 3b, E, 32.8 g was dissolved in absolute ethanol, 500 mL. The E/ethanol solution was added to the reaction flask at a rate such that the temperature remained less than 5° C. The addition was completed in 30 minutes. The reaction mixture was stirred for one hour. Toluene, 300 mL (2.823 moles), was charged to the reaction flask. Water, 500 mL, was added to the reaction mixture at a rate such that the temperature remained less than 5° C. The phases were separated and the organic phase was washed with water, 100 mL. The phases were separated and the toluene solution of the product (±)-α-(2-chlorophenyl)-α-[2-[1-methylethyl)amino]ethyl]piperidine-1-butanenitrile, F was held in a toluene solution for the next step.

Step 3d

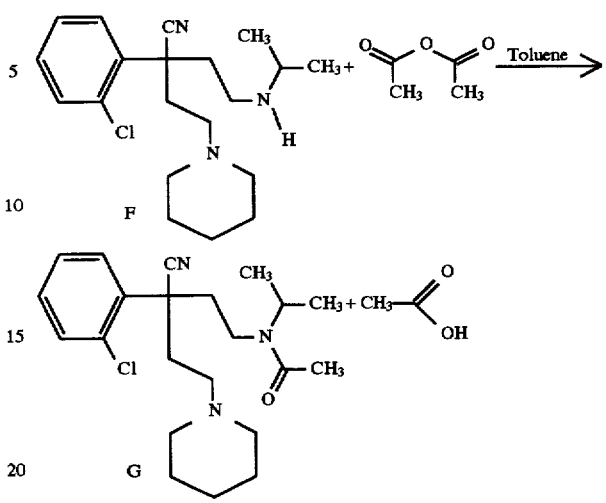

A 1-L, 4-neck round bottom reaction flask was equipped with a condenser, thermometer, mechanical stirrer, 250-mL addition funnel, and nitrogen blanket. The flask was purged with nitrogen. The product of Step 3c, F, dissolved in toluene, 300 mL, was charged to the reaction flask. The reaction flask was charged with acetic anhydride, 20 mL (0.212 mole) and the reaction mixture was stirred for one hour. The reaction was quenched by adding ethanol, 10 mL (0.172 mole), to the reaction mixture. The reaction mixture was stirred for 15 minutes. Water, 50 mL, was added to the product solution. Potassium carbonate, 35.0 g, was dissolved in water, 150 mL. The potassium carbonate/water solution was charged to the reaction mixture at a rate such that the temperature remained below 25° C. The reaction mixture was stirred for 15 minutes. The phases were separated. The organic phase was dried with potassium carbonate, 15 g. The mixture was filtered and the filtrate was stripped of solvent under vacuum at 50° C. The product, (±)-N-[3-(2-chlorophenyl)-3-cyano-5-(1-piperidinyl)pentyl]-N-(1-methylethyl)acetamide, G was recovered as a viscous orange oil, 32.4 g and was carried directly into the next reaction.

Step 4

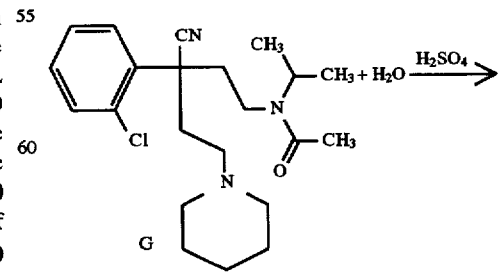

13
-continued

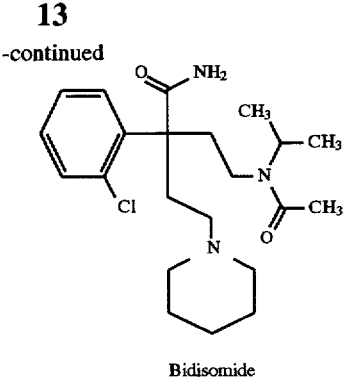

Bidisomide

A 1-L, 4-neck round bottom reaction flask was equipped with a condenser, thermometer, mechanical stirrer, 250-mL addition funnel, nitrogen blanket, and heating mantle. The reaction flask was purged with nitrogen. Sulfuric acid, 46.7 mL (0.841 mole) was charged to the reaction flask. The reaction mixture was stirred and heated to 75° C. Heptane, 30 mL was added to the product of Step 3d, G, and thoroughly mixed to obtain a homogenous mixture. The G/heptane was added to the reaction mixture at a rate such that the temperature remained at 75° C. The addition was completed in 30 minutes. A dark brown viscous solution resulted which was stirred at 75° C. for two hours. The solution was sampled for TLC analysis. The reaction was complete as indicated by the disappearance of G. The reaction mixture was cooled to 35° C. and water, 140 mL, was added to the reaction mixture at a rate such that the temperature did not exceed 40° C. The addition was completed in one hour. Then 50% NaOH solution, 84.0 mL (1.592 moles) was added to the reaction mixture at a rate such that the temperature did not exceed 45° C. The addition was completed in one hour. Ethyl acetate, 155 mL, was charged to the reaction mixture and stirred for 15 minutes while maintaining the temperature at 45° C. The phases were separated. The aqueous and interface phases were returned to the reaction flask and stirred at 45° C. Ethyl acetate, 80 mL, was added to the aqueous phase and stirred for 15 minutes while maintaining the temperature at 45° C. The phases were separated. The organic phases were combined and the solvent was then stripped from the product solution at 50° C. under vacuum to give crude product. Ethyl acetate, 235 mL, was added to the crude product and the mixture was heated to reflux. The resulting hot solution was filtered through a preheated fritted glass funnel. The fritted glass funnel was rinsed with the refluxing ethyl acetate, 60 mL, and the rinse was combined with the product solution in a reaction flask equipped with a mechanical stirrer, thermometer, heating mantle, thermowatch, Dean-Stark apparatus, condenser, and nitrogen blanket. The reaction mixture was stirred and heated to reflux. Ethyl acetate, 60 mL, was removed by distillation using the Dean-Stark apparatus. The reaction mixture was cooled to 40° C. and stirred for one hour. Crystallization occurred forming white crystals. The solution became viscous and was cooled to ambient temperature, and stirred for one hour. The mixture was then cooled to less than 5° C. using an ice water bath and stirred for one hour. The product solution was filtered and the filter cake were rinsed with cold, (less than 5° C.) ethyl acetate, 2*30 mL. The wet filter cake was charged into a crystallizing dish and dried in an oven at 50° C. under vacuum. Pure bidisomide 19.5 g, (54.8% yield based on intermediate C) was recovered as white crystals. The product was shown to be a single pure component by thin layer chromatographic analysis.

14

I claim:

1. A process for the preparation of a compound of the formula

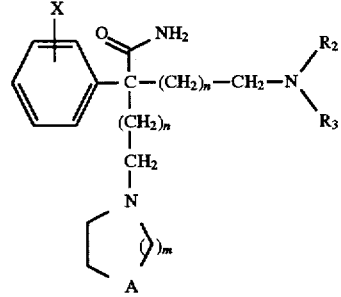

or the pharmaceutically acceptable acid addition salts thereof wherein X is selected from the group consisting of halo, alkyl having 1 to 6 carbon atoms, hydrido, trifluoromethyl, phenyl, and lower alkoxy having 1 to 6 carbon atoms; A is selected from the group consisting of $CH_2$ and O; $R_2$ is alkyl having 1 to 6 carbon atoms; $R_3$ is selected from the group consisting of acetyl, benzoyl, phenacetyl and trifluoroacetyl; m is an integer 1 or 2 and n is an integer from 1 to 3 inclusive; which comprises:

(a) reacting a halogenated alkyl N-containing heterocycle of the formula

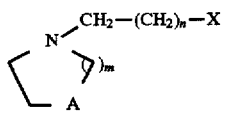

with a halogenated benzeneacetonitrile

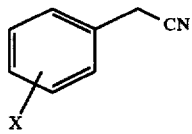

in the presence of a base and methyltributylammonium chloride to produce an α-(halophenyl)-1-N-containing heterocyclealkanenitrile of the formula

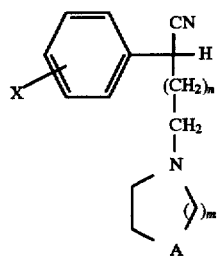

(b) alkylating the α-(halophenyl)-1 N-containing heterocyclealkanenitrile with an alkylating agent in the presence of a base and DMSO to produce an alkylated N-containing heterocyclealkanenitrile of the formula

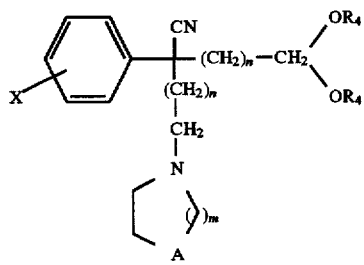

wherein $R_4$ is an alkyl having 1 to 6 carbon atoms;

(c) hydrolyzing the alkylated N-containing heterocyclealkanenitrile in an inert solvent with hydrochloric acid to produce an N-containing heterocyclealkanenitrile of the formula

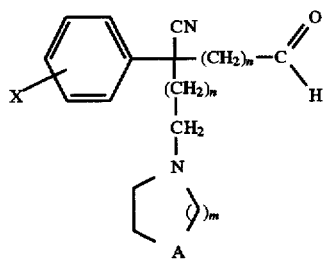

(d) reacting the resulting N-containing heterocyclealkanenitrile with an alkylamine in a solvent to produce an imine of the formula

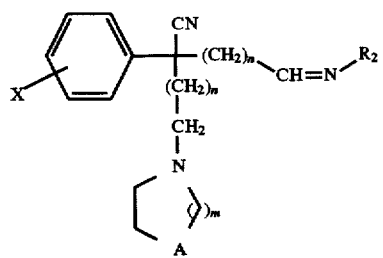

wherein $R_3$ is an alkyl of 1 to 6 carbon atoms;

(e) reducing the imine with sodium borohydride in ethanol to produce an amine of the formula

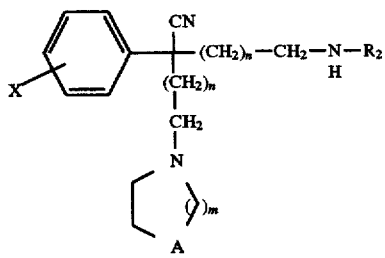

(f) acylating the amine with an acylating agent in a solvent to produce an acylated amine of the formula

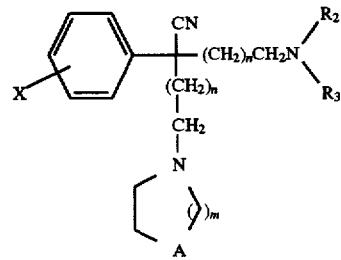

wherein $R_2$ is selected from the group consisting of acetyl, benzoyl, phenacetyl and trifluoroacetyl;

(g) hydrolyzing the acylated amine with sulfuric acid to produce an N-containing heterocycle-alkanamide of the formula

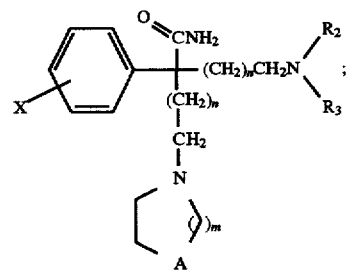

and (h) recovering the N-containing heterocycle-alkanamide.

2. A process according to claim 1 for preparing a compound of the formula

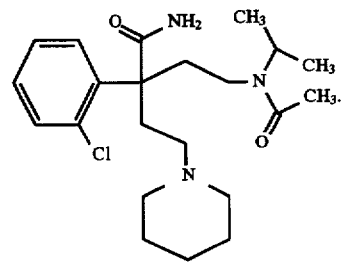

3. A process according to claim 1 wherein the alkylating agent is selected from the group consisting of bromoacetaldehyde dimethyl acetal, chloroacetaldehyde dimethyl acetal, 2-(2-bromoethyl)-1,3-dioxolane, chloroacetaldehyde diethyl acetal and bromoacetaldehyde diethyl acetal.

4. A process according to claim 3 wherein the alkylating agent is bromoacetaldehyde dimethyl acetal.

5. A process according to claim 4 wherein the alkylamine is isopropylamine.

6. A process according to claim 5 wherein the inert solvent used in Step (c) is toluene.

7. A process according to claim 6 wherein the base used in Step (a) is sodium hydroxide.

8. A process for the preparation of a compound of the formula

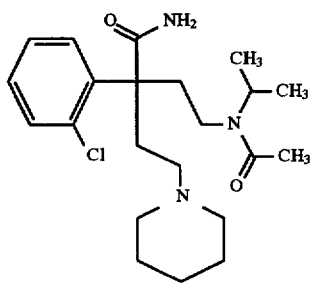

which comprises (a) reacting 2-chlorobenzeneacetonitrile with 1-(2-chloroethyl)piperidine in the presence of a base and DMSO to produce a piperidinebutanenitrile of the formula

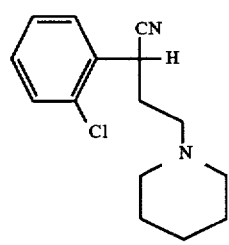

(b) alkylating the resulting piperidinebenzene-butanenitrile with an alkylating agent in the presence of a base and DMSO to produce a piperidinebutanenitrile of the formula

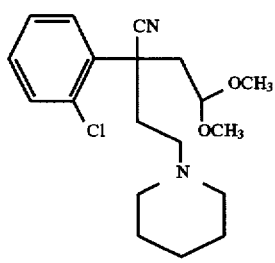

(c) hydrolyzing the resulting piperidine-butanenitrile in toluene with hydrochloric acid to produce a compound of the formula

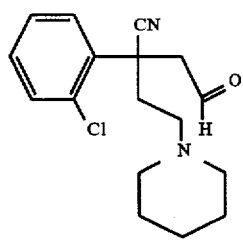

(d) reacting the resulting compound with isopropylamine in a solvent to form an imine of the formula

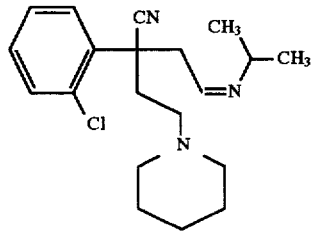

(e) reducing the imine with sodium borohydride in ethanol to form an amine of the formula

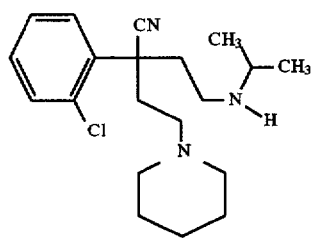

(f) acetylating the resulting amine with acetic anhydride in a solvent to produce an acetylated amine of the formula

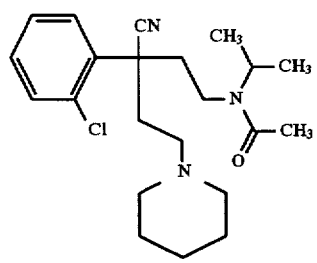

(g) hydrolyzing the acetylated amine with sulfuric acid to produce

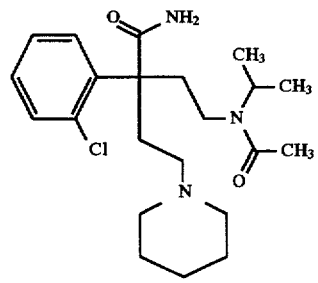

(h) recovering the compound so produced.

9. A process according to claim 8 wherein the base used in step (a) is sodium hydroxide.

10. A process according to claim 9 wherein the alkylating agent used in step (b) is bromoacetaldehyde dimethyl acetal.

11. A process according to claim 10 wherein the base used in step (b) is potassium hydroxide.

12. A process according to claim 11 wherein the solvent used in step (d) is toluene.

13. A process according to claim 12 wherein the solvent used in step (f) is toluene.

* * * * *